(12) United States Patent
Chaudhry

(10) Patent No.: US 10,820,861 B2
(45) Date of Patent: Nov. 3, 2020

(54) ENDOTRACHEAL TUBES AND SYSTEMS AND METHODS FOR EVALUATING BREATHING

(71) Applicant: H. LEE MOFFITT CANCER CENTER AND RESEARCH INSTITUTE, INC., Tampa, FL (US)

(72) Inventor: Tariq Chaudhry, Tampa, FL (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 186 days.

(21) Appl. No.: 15/125,789

(22) PCT Filed: Mar. 13, 2015

(86) PCT No.: PCT/US2015/020493
§ 371 (c)(1),
(2) Date: Sep. 13, 2016

(87) PCT Pub. No.: WO2015/138932
PCT Pub. Date: Sep. 17, 2015

(65) Prior Publication Data
US 2017/0367653 A1    Dec. 28, 2017

Related U.S. Application Data

(60) Provisional application No. 61/953,193, filed on Mar. 14, 2014.

(51) Int. Cl.
*A61B 5/00* (2006.01)
*A61M 16/04* (2006.01)
*A61B 5/08* (2006.01)

(52) U.S. Cl.
CPC .............. *A61B 5/6853* (2013.01); *A61B 5/08* (2013.01); *A61B 5/4878* (2013.01); *A61M 16/04* (2013.01);
(Continued)

(58) Field of Classification Search
CPC .......... A61M 16/0427; A61M 16/0475; A61M 16/0479; A61M 16/0486; A61M 16/04;
(Continued)

(56) References Cited

U.S. PATENT DOCUMENTS 5,193,533 A * 3/1993 Body ................ A61M 16/0418
128/207.14
5,702,365 A * 12/1997 King ..................... A61M 29/02
604/105
(Continued)

FOREIGN PATENT DOCUMENTS

WO       2013/109569         7/2013

OTHER PUBLICATIONS

International Search Report and Written Opinion issued in International Application No. PCT/US15/20493, dated Jun. 16, 2015.

*Primary Examiner* — Peter S Vasat
(74) *Attorney, Agent, or Firm* — Meunier Carlin & Curfman LLC

(57) ABSTRACT

The present application relates to endotracheal tubes and to systems and methods for detecting airway edema and evaluating breathing with an endotracheal tube. An example endotracheal tube includes a distal portion, a proximal portion, and a linker portion. The linker portion couples the distal portion and the proximal portion. The linker portion includes at least two struts. The struts extend between the distal portion and the proximal portion. Also, there is at least one opening defined between and along the length of the struts. The linker portion is configured to contact the vocal cords of the subject when in use.

15 Claims, 4 Drawing Sheets

(52) U.S. Cl.
CPC .... *A61M 16/0402* (2014.02); *A61M 16/0434* (2013.01)

(58) Field of Classification Search
CPC .......... A61M 16/0402; A61M 16/0434; A61M 1/0078; A61M 16/0411; A61M 16/0429; A61M 2005/1588; A61M 25/0021; A61M 2025/0025; A61M 25/0041; A61M 25/0043; A61M 25/0054; A61M 25/0029; A61M 2025/0034; A61B 5/08; A61B 5/4878; A61B 5/6853; A61B 2090/701; A61F 2002/046
See application file for complete search history.

(56) References Cited

U.S. PATENT DOCUMENTS

| | | | | |
|---|---|---|---|---|
| 6,634,360 | B1* | 10/2003 | Flodin | A61M 1/0001 128/207.14 |
| 2010/0317956 | A1* | 12/2010 | Kartush | A61B 5/04001 600/380 |
| 2011/0190596 | A1 | 8/2011 | Hacker et al. | |
| 2013/0098358 | A1* | 4/2013 | Blom | A61M 16/0488 128/200.26 |

\* cited by examiner

ENDOTRACHEAL TUBES AND SYSTEMS AND METHODS FOR EVALUATING BREATHING

CROSS-REFERENCE TO RELATED APPLICATIONS

This application claims the benefit of priority to U.S. Provisional Patent Application No. 61/953,193 filed Mar. 14, 2014, the disclosure of which is incorporated herein by reference in its entirety.

TECHNICAL FIELD

This present application relates to endotracheal tubes and to systems and methods for evaluating laryngeal breathing and its effect on spontaneous breathing.

BACKGROUND

During medical procedures, both surgical and non-surgical, patients must be intubated. Various medical conditions and prolonged intubations can cause swelling of the airway.

While intubated, an endotracheal tube overcomes any airway swelling and allows the free flow of the ventilator gases. During extubation, however, the presence of airway swelling can lead to an airway compromise requiring urgent re-intubation.

SUMMARY

Provided are systems and method for evaluating breathing with a modified endotracheal tube. The details of one or more embodiments of the disclosure are set forth in the accompanying drawings and the description below. Other features, objects, and advantages of the disclosure will be apparent from the description and drawings, and from the claims.

Provided herein are endotracheal tubes. An example endotracheal tube includes a distal portion, a proximal portion, and a linker portion. The linker portion couples the distal portion and the proximal portion. The linker portion includes at least two struts. The struts extend between the distal portion and the proximal portion. Also, there is at least one opening defined between and along the length of the struts. The linker portion is configured to contact the vocal cords of the subject when in use.

Also provided herein is a method for evaluating breathing in a subject. This method involves positioning the disclosed endotracheal tube in the subject. The method can also involve positioning a stent through the lumen of the proximal portion, through the linker portion, and into the lumen of the distal portion. The method can further involve removing the stent from the distal portion and linker portion. The method can also involve determining breathing characteristics of the subject. The breathing characteristics can be determined after removal of the stent from the distal and the linker portions.

DESCRIPTION OF DRAWINGS

Like reference symbols in the various drawings indicate like elements.

DETAILED DESCRIPTION

Figure 1:
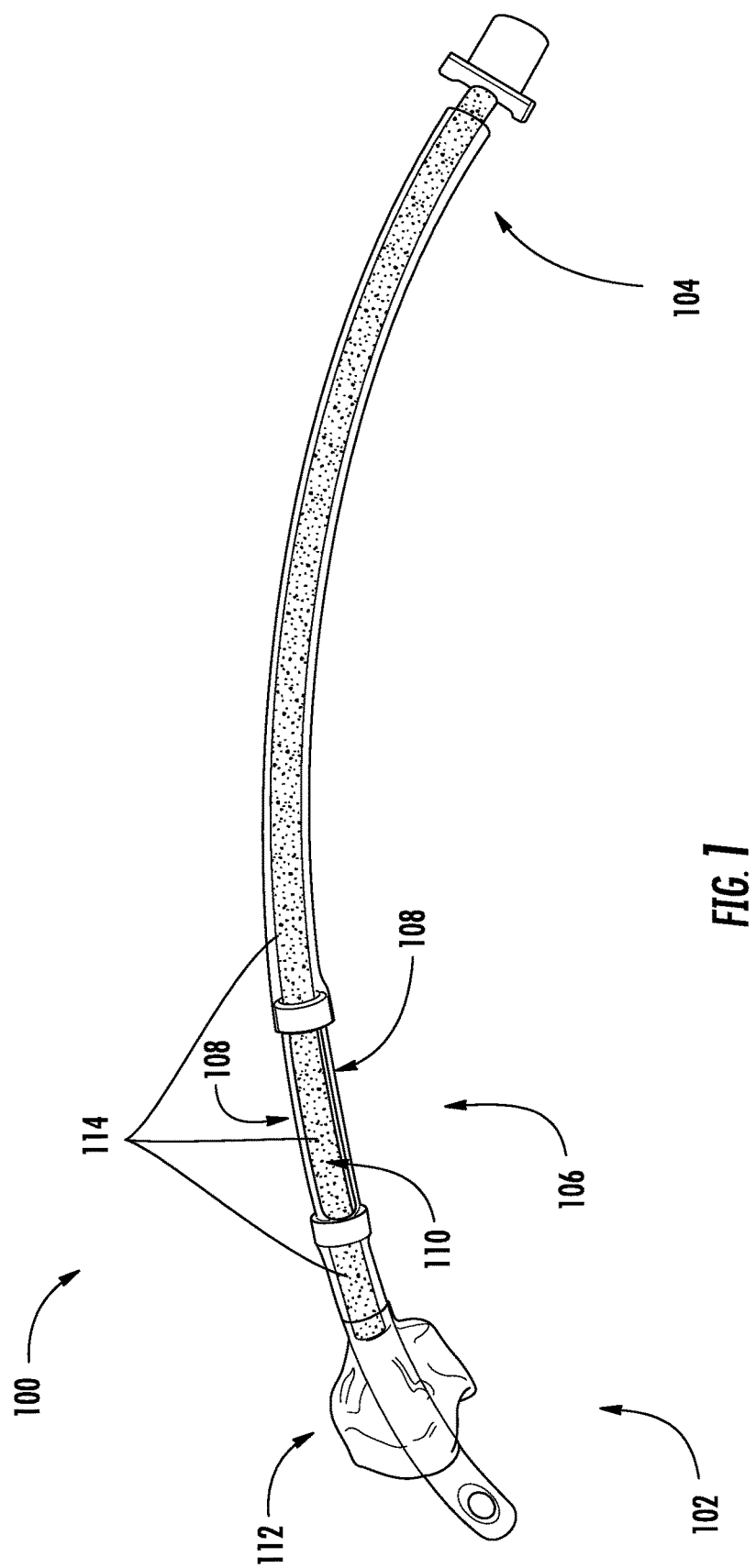
FIG. 1 is a perspective view of an endotracheal tube with a inserted stent, in accordance with the present disclosure.

The following is a description of several illustrations of the subject matter of Applicant's invention. Certain terminology is used herein for convenience only and is not to be taken as a limitation on the present invention. In the drawings, the same reference numbers are employed for designating the same elements throughout the several figures. A number of examples are provided, nevertheless, it will be understood that various modifications can be made without departing from the spirit and scope of the disclosure herein. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms.

The present invention now will be described more fully hereinafter with reference to specific embodiments of the invention. Indeed, the invention can be embodied in many different forms and should not be construed as limited to the embodiments set forth herein; rather, these embodiments are provided so that this disclosure will satisfy applicable legal requirements.

Patients are intubated when undergoing an array of medical procedures, including both surgical and non-surgical procedures. Under prolonged intubations, a patient may experience airway edema and/or swelling. Furthermore, certain medical conditions, such as obesity, can cause airway edema. While intubated, a commonly-used endotracheal tube overcomes any airway swelling that may be present to allow the free-flow of the ventilator gases.

In the presence of airway swelling, extubation is risky and can lead to an airway compromise requiring urgent re-intubation. Aside from clinical judgment by a medical professional, no test accurately predicts airway swelling. In order for a medical professional to make a clinical judgment regarding airway swelling, an intubated patient must be fully awake. Thus, sedatives at this point may not be used because the patient needs to be cooperative and able to follow commands. The high level of anxiety in awake and intubated patients can lead to hypertension and tachycardia, potentially complicating the existing medical conditions.

In the event that a patient is prematurely extubated, the clinical and professional management of this premature extubation adds to the medical expenses in the form of medications, medical supplies, equipment, and personnel. On the other hand, a more conservative extubation approach leads to an unnecessarily prolonged intubation, which also adds to the medical expenses in acute-care facilities.

Provided herein are systems and methods for detecting airway edema and evaluating breathing with a modified endotracheal tube. Such systems and methods can be used, for example, to intubate patients and evaluate breathing during the extubation process. For example, provided is an endotracheal tube used to assess airway edema and swelling in intubated patients. This endotracheal tube can help medical professionals assess airway flow in intubated patients.

Figure 2:
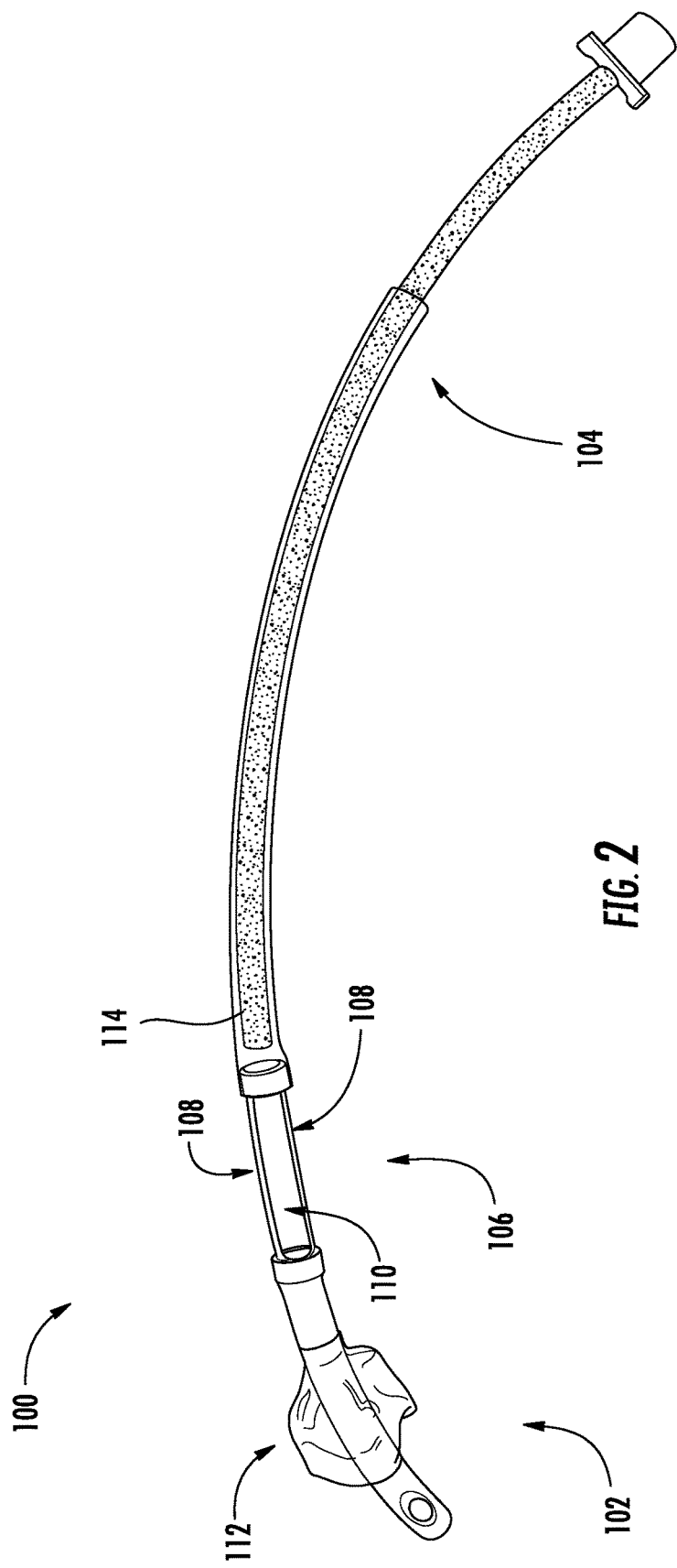
FIG. 2 is a perspective view of an endotracheal tube with a partially inserted stent, in accordance with the present disclosure.
Figure 3:
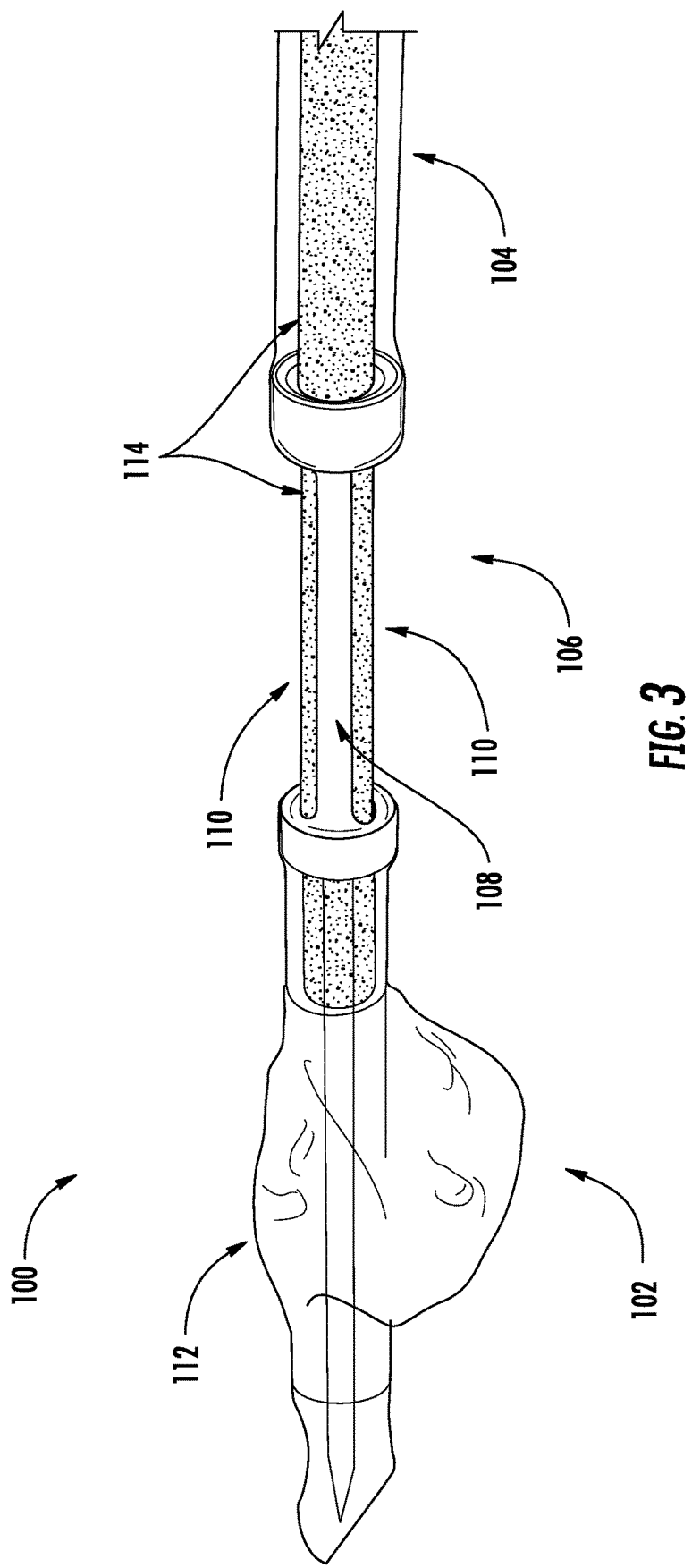
FIG. 3 is a perspective view of an endotracheal tube with an inserted stent, in accordance with the present disclosure.
Figure 4:
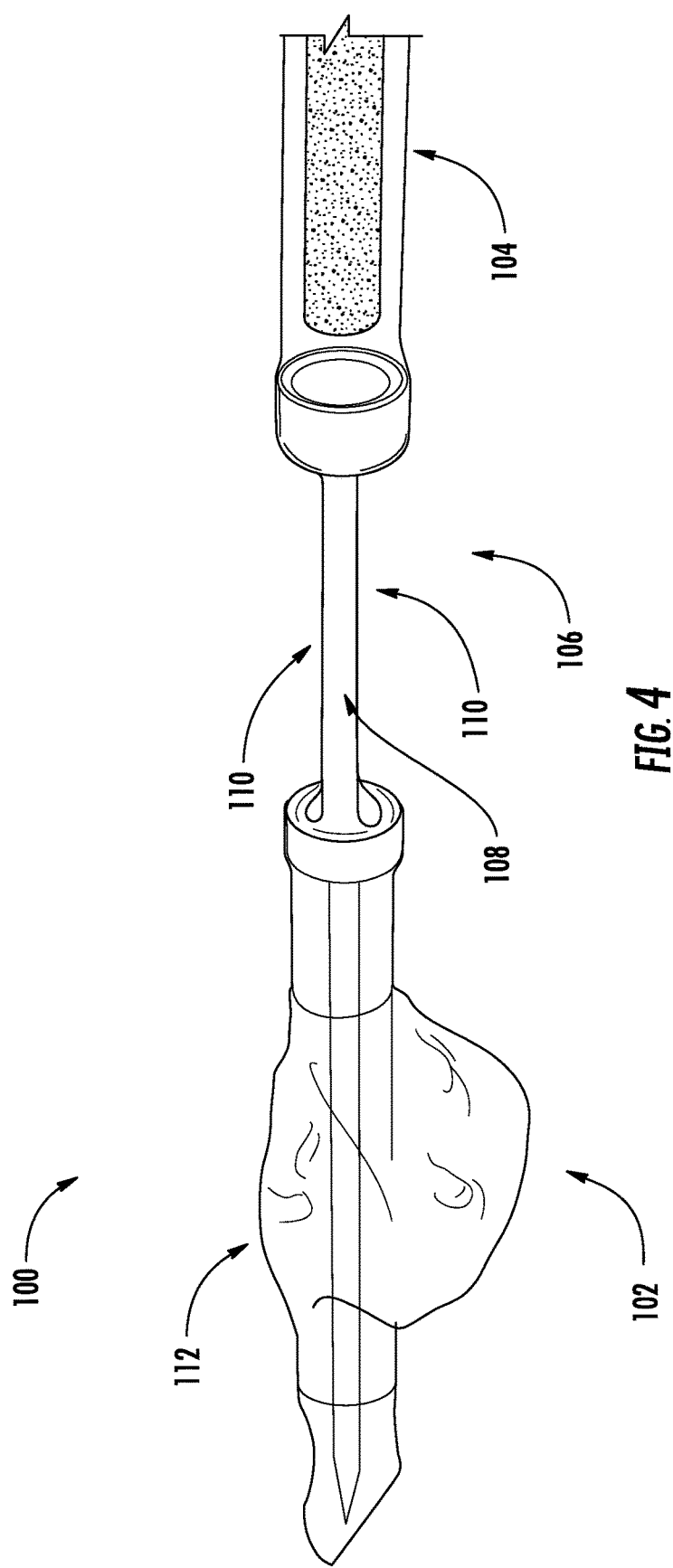
FIG. 4 is a perspective view of an endotracheal tube with a partially inserted stent, in accordance with the present disclosure.

FIGS. 1-4 show an example of a disclosed endotracheal tube 100. The endotracheal tube 100 includes a distal portion 102, a proximal portion 104, and a linker portion 106. The linker portion 106 couples the distal portion 102 and the proximal portion 104. Optionally, the proximal portion 104 and the distal portion 102 are axially aligned. The distal portion 102 and the proximal portion 104 can comprise standard endotracheal tubing structure. The linker portion 106 is optionally configured to be positioned at the vocal cords of a subject after intubation of the endotracheal tube 100.

The linker portion 106 of the example endotracheal tube 100 can include at least two struts 108. These struts 108 extend between the distal portion 102 and the proximal portion 104. Additionally, the struts 108 define an opening 110 between and along the length of the struts 108. Optionally the struts 108 can be rigid, semi rigid, compressible, or bendable. For example, the struts 108 can be bendable by pressure from swollen subject tissue. Optionally, the struts 108 are configured to be displaced. For example, the struts 108 can displace towards the midline of the linker portion 106. This displacement can be caused, for example, by pressure from edematous laryngeal tissue. Optionally, the linker 106 portion is at least 1 inch in length, such as about 2 inches or more in length. Furthermore, the linker portion 106 can be formed from any suitable medical grade material, including medical plastic.

An example endotracheal tube 100 can optionally include a stent 114. For example, the stent 114 can be an elongated tubal device. The stent 114 is optionally formed from a PVC-type material, a metal, or any other suitable material. The outer circumference of the tubal stent is optionally less than the inner circumference of the endotracheal tube 100, such that the stent 114 can fit inside the endotracheal tube 100 lumen. Optionally, the ratios of the circumferences are such that the stent 114 can slide freely within the endotracheal tube 100 with an appropriate amount of friction. For example, an operator can advance or withdraw the stent 114 through the lumen of the proximal portion 104, through the linker portion 106, and into the lumen of the distal portion 104. The stent 114 is optionally configured to contact the vocal chords through opening 110 between and along the length of the struts 108 when inserted through the lumen of the linker 106 portion.

The disclosed endotracheal tube 100 can be configured to deliver a gas to the subject. The gas can be delivered, for example, through the endotracheal tube 100 and/or the stent 114. Additionally, the displacement of the struts 108 can also indicate a reduction of airflow through the linker portion 106.

Within the airway, the vocal cords comprise the narrowest opening. The linker portion 106 can be configured to reside at the vocal cords when the endotracheal tube 110 is positioned. The proximal portion 104 of the endotracheal tube 100 that remains outside of the subject is optionally marked to indicate to the operator or medical professional how much of the endotracheal tube 100 has been inserted into the subject. Therefore, the medical professional can assess when the linker portion 106 of the endotracheal tube 100 is positioned at the vocal cords. The operator or medical professional has flexibility to move the endotracheal tube 100 into or out of the subject, so that the linker portion 106 seats between the vocal cords.

An example endotracheal tube 100 can optionally include an inflatable cuff 112. The inflatable cuff 112 can be positioned about the endotracheal tube 100. Optionally, the inflatable cuff 112 can be positioned along the distal portion 102 of the endotracheal tube 100. The cuff 112 can optionally be inflated or deflated by an operator. Under normal clinical conditions, the cuff 112 is deflated during the intubation procedure of a patient, so that an endotracheal tube 100 can be inserted into the patient. Once the endotracheal tube 100 is correctly positioned in the patient, the operator of the cuff may inflate the cuff 112. Once inflated, the cuff 112 impedes flow of gasses into or out of the patient. Instead, a mechanical ventilator can distribute gasses to and from the patient through the endotracheal tube 100. Prior to extubation, the cuff 112 is deflated. After deflation of the cuff, the cuff 112 and endotracheal tube 100 may be removed from the patient.

Also provided in the present application is a method for evaluating breathing in a subject. Under this method, a patient is intubated with the disclosed endotracheal tube 100 without any modified intubation techniques, and there are no modifications necessary for the ventilator settings or ventilator management. During extubation and with the described tubes and systems, the patient's ability to comfortably breathe after the stent 114 is removed from the linker portion 106 reflects an airway that is suitable for a safe extubation. However, if there is swelling of the airway after the stent 114 is removed, it can deform the struts 108 and reduce breathing through the endotracheal tube 100. In the event that swelling of the airway is present, breathing characteristics, such as stridor, signals to the medical professionals present that extubation should not proceed. The patient should thus be placed back on mechanical ventilation. In extreme cases, no breathing occurs after a patient is extubated and must be placed back on mechanical ventilation.

The method for evaluating the breathing of a subject includes positioning an endotracheal tube 100 in the subject. The endotracheal tube 100 has a distal portion 102, a proximal portion 104, and a linker portion 106. The linker portion 106 couples the distal portion 102 and the proximal portion 104. The linker portion 106 includes at least two struts 108. The struts 108 extend between the distal portion 102 and the proximal portion 104. Also, there is at least one opening 110 defined between and along the length of the struts 108. The linker portion 106 can be configured to contact the vocal cords of the subject after the endotracheal tube 100 is positioned. The method can also include positioning a stent 114 through the lumen of the proximal portion 102, through the linker portion 106, and into the lumen of the distal portion 104 during mechanical ventilation. The method can also includes removing the stent 114 from the distal portion and linker portion 104, 106 prior to extubation. The method also includes determining breathing characteristics of the subject. The breathing characteristics can be determined after removal of the stent from the distal and the linker portions 104, 106.

Optionally the evaluation of the breathing indicates that the subject is able to breathing without intubation. Then the method can include removing the endotracheal tube 100 from the subject. Optionally, the evaluation of the breathing indicates that the subject is not able to breathe without intubation. For example, the subject has airway edema, prolonged intubation, vocal cord injury, obesity, prolonged head down procedures, difficult airway, or any pediatric procedure requiring an intubation. Optionally, the method includes the evaluation of breathing of a subject to determine that the subject has airway edema or vocal cord injury. The method can then include repositioning the stent 114 into the lumen of the linker portion 106.

A number of embodiments of the invention have been described. Nevertheless, it will be understood that various modifications may be made without departing from the spirit and scope of the invention. Accordingly, other embodiments are within the scope of the following claims.

Disclosed are materials, systems, devices, compositions, and components that can be used for, can be used in conjunction with, can be used in preparation for, or are products of the disclosed methods, systems and devices. These and other components are disclosed herein, and it is understood that when combinations, subsets, interactions, groups, etc. of these components are disclosed that while specific reference of each various individual and collective combinations and permutations of these components may not be explicitly disclosed, each is specifically contemplated and described herein. For example, if a method is disclosed and discussed each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed systems or devices. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the materials for which they are cited are hereby specifically incorporated by reference in their entireties.

What is claimed is:

1. An endotracheal access system for detecting airway edema and evaluating breathing comprising:
   an endotracheal tube comprising a distal portion, a proximal portion, and a linker portion that couples the distal portion and the proximal portion, wherein the proximal portion defines a lumen and the distal portion defines a lumen, wherein the linker portion includes at least two struts that extend between the distal portion and the proximal portion and wherein there is at least one opening defined between and along the length of the struts, wherein an inflatable cuff is positioned about the endotracheal tube along the distal portion,
   a stent,
   wherein the stent is advanceable though the lumen of the proximal portion, through the linker portion, and into the lumen of the distal portion,
   wherein the stent is configured to contact the vocal chords through the at least one opening defined between and along the length of the struts when the stent is fully advanced through the lumen of the proximal portion, the linker portion, and into the lumen of the distal portion.

2. The endotracheal access system of claim 1, wherein the proximal portion and the distal portion are axially aligned.

3. The endotracheal access system of claim 1, wherein the struts are semi rigid.

4. The endotracheal access system of claim 3, wherein the struts are configured to displace towards a central midline of the linker portion by pressure from edematous laryngeal tissue.

5. The endotracheal access system of claim 1, wherein the struts are bendable by pressure from swollen subject tissue.

6. The endotracheal access system of claim 1, wherein displaced struts indicate a reduction in airflow through the linker portion.

7. The endotracheal access system of claim 1, wherein gas is deliverable to the subject through the endotracheal tube.

8. The endotracheal access system of claim 1, wherein the linker portion comprises medical plastic.

9. The endotracheal access system of claim 1, wherein the length of the linker portion is between about 1 inch and about 2 inches.

10. The endotracheal access system of claim 1, wherein the length of the linker portion is more than 2 inches.

11. A method for evaluating breathing in a subject, comprising:
   a. providing the endotracheal access system of claim 1;
   b. positioning the endotracheal tube in the subject wherein the linker portion contacts the vocal cords of the subject;
   c. positioning the stent through the lumen of the proximal portion, through the linker portion, and into the lumen of the distal portion;
   d. removing the stent from the distal portion and linker portion;
   e. determining breathing characteristics of a subject after removal of the stent from the distal portion and linker portion.

12. The method of claim 11, further comprising removing the endotracheal tube from the subject.

13. The method of claim 11, further comprising removing the stent from the subject.

14. The method of claim 11, further comprising removing the stent and the endotracheal tube from the subject.

15. The method of claim 11, further comprising repositioning the stent within the distal portion and linker portion.

* * * * *